United States Patent
Agarwal et al.

(10) Patent No.: US 10,449,137 B2
(45) Date of Patent: Oct. 22, 2019

(54) ANTIMICROBIAL COMPOSITION

(71) Applicant: Conopco, Inc., Englewood Cliffs, NJ (US)

(72) Inventors: Khushbu Agarwal, Bangalore (IN);
Amitabha Majumdar, Bangalore (IN);
Mruthyunjaya Swamy Mathapathi, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/060,481

(22) PCT Filed: Dec. 12, 2016

(86) PCT No.: PCT/EP2016/080544
§ 371 (c)(1),
(2) Date: Jun. 8, 2018

(87) PCT Pub. No.: WO2017/102610
PCT Pub. Date: Jun. 22, 2017

(65) Prior Publication Data
US 2018/0360724 A1 Dec. 20, 2018

(30) Foreign Application Priority Data
Dec. 14, 2015 (EP) .................... 15199792

(51) Int. Cl.
*A61K 8/34* (2006.01)
*A61K 8/64* (2006.01)
*A61K 8/67* (2006.01)
*C11D 3/20* (2006.01)
*C11D 3/32* (2006.01)
*C11D 3/48* (2006.01)
*C11D 9/26* (2006.01)
*C11D 9/30* (2006.01)
*A01N 31/04* (2006.01)
*A01N 31/08* (2006.01)
*A01N 43/40* (2006.01)
*A01N 65/22* (2009.01)
*A61K 38/17* (2006.01)
*A61Q 17/00* (2006.01)
*A61Q 19/10* (2006.01)

(52) U.S. Cl.
CPC .............. *A61K 8/675* (2013.01); *A01N 31/04* (2013.01); *A01N 31/08* (2013.01); *A61K 8/34* (2013.01); *A61K 8/347* (2013.01); *A61K 8/64* (2013.01); *A61K 38/1729* (2013.01); *A61Q 17/005* (2013.01); *A61Q 19/10* (2013.01); *C11D 3/2034* (2013.01); *C11D 3/2037* (2013.01); *C11D 3/32* (2013.01); *C11D 3/48* (2013.01); *C11D 9/26* (2013.01); *C11D 9/30* (2013.01); *A61K 2800/74* (2013.01)

(58) Field of Classification Search
None
See application file for complete search history.

(56) References Cited

U.S. PATENT DOCUMENTS

| | | |
|---|---|---|
| 5,695,573 A | 12/1997 | Becker |
| 2004/0076614 A1 | 4/2004 | Schur |
| 2008/0160070 A1 | 7/2008 | Crawford |
| 2009/0220625 A1 | 9/2009 | Herrmann |
| 2010/0047202 A1 | 2/2010 | Goddinger et al. |
| 2010/0069400 A1 | 3/2010 | Malstrom et al. |
| 2010/0222433 A1 | 9/2010 | Xue et al. |

FOREIGN PATENT DOCUMENTS

| | | |
|---|---|---|
| DE | 4401274 | 7/1995 |
| DE | 20201001395 | 11/2010 |
| WO | WO0062740 | 10/2000 |
| WO | WO07079793 | 7/2007 |
| WO | WO08025679 | 3/2008 |
| WO | WO08074576 | 6/2008 |
| WO | WO08080702 | 7/2008 |
| WO | WO2008080701 | 7/2008 |
| WO | WO2008080708 | 7/2008 |
| WO | WO10018418 | 2/2010 |
| WO | WO2010046238 | 4/2010 |
| WO | WO12020075 | 2/2012 |
| WO | WO2012177986 | 12/2012 |
| WO | WO2013017967 | 2/2013 |
| WO | WO2013083393 | 6/2013 |
| WO | WO2014037167 | 3/2014 |
| WO | WO14078849 | 5/2014 |
| WO | WO2015051260 | 4/2015 |

OTHER PUBLICATIONS

Fan et al., Pharmazie (2013), 68(7), pp. 628-630.*
Donald L. Bissett, PHD; Common Cosmeceuticals; Clinics in Dermatology; 2009; pp. 435-445; XP026471172; vol. 27, No. 5; United States of America.
IPRP in PCTEP2016080544; Nov. 23, 2017.
Popovic et al.; Peptides with antimicrobial and anti-inflammatory activities that have therapeutic potential for treatment of acne vulgaris; Peptides; 2012; pp. 275-282; XP055255645; vol. 34, No. 2; Elsevier; Serbia.
Search Report and Written Opinion in EP15199792; dated Mar. 21, 2016.
Search Report and Written Opinion in PCTEP2016080544; dated Feb. 8, 2017.

* cited by examiner

*Primary Examiner* — Brian J Davis
(74) *Attorney, Agent, or Firm* — Foley & Lardner LLP

(57) ABSTRACT

The present invention provides an antimicrobial composition comprising a) Thymol; b) Terpineol; c) Niacinamide or its derivatives thereof; and d) a cosmetically acceptable base.

16 Claims, No Drawings

ANTIMICROBIAL COMPOSITION

TECHNICAL FIELD

The present invention relates to an antimicrobial composition and a method of disinfecting a surface. The invention more particularly relates to an antimicrobial composition that provides prolonged/long-lasting antimicrobial benefits.

BACKGROUND OF THE INVENTION

People try to take good care of the external surface of their bodies as well as those of their pets to enable good overall health. Specific skin related issues that people care about include, good skin health free of infections, good skin tone and skin hygiene. Skin hygiene is generally achieved by keeping them free of infections. One way to tackle infections is to treat them with antimicrobials after the infection has set in. Another approach is to leave a minimal amount of antimicrobial active on the surface so that any invading microorganism is killed or inactivated so as to minimize spread of disease. Yet another approach is improving the innate immunity of the desired surface.

There are different antimicrobial compositions known in the art;

WO 2010/046238 (Unilever, 2010) discloses an antimicrobial composition for cleansing or personal care. It is an object of the present invention to provide antimicrobial compositions that have relatively fast antimicrobial action. Present inventors have surprisingly found that compositions comprising selected ingredients, namely thymol and terpineol, in selective propositions provide relatively quick antimicrobial action.

WO 13/017967 (KIMBERLY CLARK, 2013) discloses an antimicrobial cleansing composition comprising: a polar carrier solvent; from about 0.1 percent (w/w) to about 15 percent (w/w) cationic compatible surfactant; from about 0.01 percent (w/w) to about 10 percent (w/w) quaternary ammonium biocide; and a cationic compatible afterfeel agent, wherein the antimicrobial cleansing composition is substantially free of a betaine-based surfactant and substantially free of a compound selected from the group consisting of triclosan, triclocarban, a halogenated phenolic antimicrobial agent, and combinations thereof.

US 2010 222433 (SHANGHAI JIUYU BIOLOGICAL TECHNOLOGY, 2010) Discloses A composite disinfectant cleaner which, on a total composition weight basis, comprises: (a) about 0.5-0.7 weight percent of an alkyl dimethyl benzyl ammonium chloride (b) about 0.3-0.5 weight percent of an octyl decyl dimethyl ammonium chloride (c) about 0.1-0.2 weight percent of a dioctyl dimethyl ammonium chloride (d) about 0.2-0.3 weight percent of a didecyl dimethyl ammonium chloride (e) about 0.5-2 weight percent of an alkylamine (f) about 0.3-1.5 weight percent of a guanidine (g) about 10-20 weight percent of a penetrant (h) about 5-10 weight percent of a surfactant (i) about 0.1-0.6 weight percent of a chelant (j) about 0.05-0.1 weight percent of an essence (k) the balance being deionized water.

WO 15051260 (Crawford Keith D, 2015) discloses Compositions, methods, and kits are provided for regenerating or treating skin cells using a composition with a biologic such as an antimicrobial peptide (AMP). The composition includes at least one of: a safe and effective amount of a vitamin B3 molecule; silicone elastomer; antioxidant; and a dermatologically acceptable carrier. The AMP is, for example, H2A, H1, H6, HDL, Sal-2, a defensin, a hepcidin, an apidaecin, a cathelicidin, or a piscidin. The AMP includes, for example, a peptide represented by the formula: APKAMX1X2X3X4X5X6X7X8LQKKGI, such that X1 and X8 represent basic amino acid residues; X2 and X3 represent hydrophobic amino acid residues which may be the same or different residues; X4 and X5 represent basic amino acid residues which may be the same or different residues; X6 and X7 represent hydrophobic amino acid residues which may be the same or different residues.

Specifically in the present days the number of contagious diseases are spreading more rapidly as we are exposed to social life like never before. We greet people by shaking hands and then we use the same hands for eating foods. Therefore there is always a chance of spreading contagious disease causing microbes from one person to another either through hand or any other kinds of contact. Therefore in the current days there is a need for an antimicrobial composition which provides prolonged/long-lasting antimicrobial benefits. Furthermore we have found that some of the antimicrobial agents though good, however because of their unpleasant attributes like smell are not very attractive at higher concentration. Also higher concentration of antimicrobial agent tends to kill the microorganisms which are believed to be beneficial for skin health.

It is therefore an object of the present invention to provide an antimicrobial composition.

It is another object of the present invention to provide an antimicrobial composition with prolonged/long-lasting benefits.

It is a further object of the present invention to provide an antimicrobial composition wherein the amount of known antimicrobial agents are minimized.

It is yet another object of the present invention to provide a topical composition that provides innate immunity to a topical surface of a human or animal body.

The present inventors have surprisingly found out that an antimicrobial composition which comprises very less amount of thymol and terpineol along with a specific amount of Niacinamide or its derivatives thereof is able to provide prolonged/long-lasting antimicrobial benefits and thereby satisfying one or more of the objects of the invention. Furthermore it is observed that further presence of an Antimicrobial peptide (AMP) actually boosts the antimicrobial property of the composition.

SUMMARY OF THE INVENTION

In a first aspect of the present invention there is provided an antimicrobial composition comprising:
 a) Thymol;
 b) Terpineol;
 c) Niacinamide or its derivatives thereof; and
 d) a cosmetically acceptable base.

In a second aspect of the present invention there is provided a method of cleaning or disinfecting a surface comprising the steps of applying a composition of the first aspect on to said surface.

Any feature of one aspect of the present invention may be utilized in any other aspect of the invention. The word "comprising" is intended to mean "including" but not necessarily "consisting of" or "composed of." In other words, the listed steps or options need not be exhaustive. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The present invention provides an antimicrobial composition comprising:

a) Thymol;
b) Terpineol;
c) Niacinamide or its derivatives thereof; and
d) a cosmetically acceptable base.

Antimicrobial composition as mentioned herein above preferably means any composition which is capable of killing or at least cause substantial reduction of the common disease causing microbes. The common disease causing gram-positive organisms includes *Staphylococcus, Streptococcus* and *Enterococcus* spp. Some of common disease causing gram-negative organisms includes *Escherichia coli, Salmonella, Klebsiella* and *Shigella. Escherichia coli* and *Salmonella* can cause severe gastrointestinal illnesses.

Thymol;

The antimicrobial composition of the present invention comprises thymol. The amount of thymol preferably is in the range of 0.001 to 5%, more preferably 0.001 to 1% and further more preferably 0.001 to 0.1% and most preferably 0.001 to 0.05%. The composition of the present invention are able to provide the required antimicrobial benefit at very low concentration of thymol. At concentrations higher than the higher preferred concentrations of thymol, when in combination with terpineol, while the kinetics of action would not be compromised, the present inventors have found that unlike in therapeutic/pesticidal/herbicidal applications where sensorial aspects are not critical, in the present application, which is preferably a personal care applications, the product is in contact with hands or other body parts, the sensorial aspects like smell and skin feel would be compromised. Thymol may be added to the antimicrobial composition in purified form.

The amount of thymol used in the composition of the present invention is preferably very low. The present inventors have found that at the low concentration of thymol when combine with the other essential ingredients of the composition able to provide prolonged/long-lasting antimicrobial action.

Alternatively, thyme oil or thyme extract comprising thymol may be added to the antimicrobial composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide,* and *Thymus citriodorus*. The isomer of thymol (carvacrol) may also preferably be used.

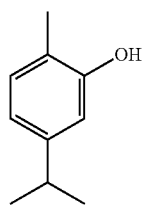

Carvacrol

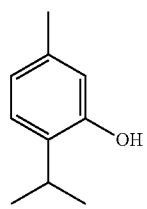

Thymol

Alternatively any derivatives of thymol which has similar properties of thymol may also preferably be used.

Terpineol:

The antimicrobial composition of the present invention also comprises terpineol. The amount of terpineol preferably is in the range of 0.001 to 5%, more preferably 0.001 to 1% and further more preferably 0.001 to 0.1% and most preferably 0.001 to 0.05%. The composition of the present invention are able to provide the required antimicrobial benefit at very low concentration of terpineol. At concentrations higher than the higher preferred concentrations of terpineol, when in combination with thymol, while the kinetics of action would not be compromised, the present inventors have found that unlike in therapeutic/pesticidal/herbicidal applications where sensorial aspects are not critical, in the present application, which is preferably a personal care applications, the product is in contact with hands or other body parts, the sensorial aspects like smell and skin feel would be compromised. Terpineol may be added to the antimicrobial composition in purified form.

The amount of terpineol used in the composition of the present invention is preferably very low. The present inventors have found that at the low concentration of terpineol when combine with the other essential ingredients of the composition able to provide prolonged/long-lasting antimicrobial action.

The structure of a terpineol is given below:

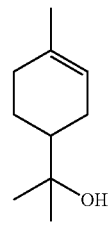

Alternatively pine oil comprising terpineol may be added to the antimicrobial composition.

Optionally, any derivatives of thymol which has similar properties of thymol may also preferably be used.

Niacinamide or its derivatives:

One of the component of the composition of the present invention is Niacinamide or its derivatives. Niacinamide is also known as Nicotinamide or Nicotinic acid amide or vitamin B3. It is a water soluble vitamin having the following structure:

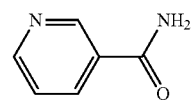

Niacinamide has anti-inflammatory actions. This is also known for treating acne. For the purpose of the present invention Niacinamide or its derivatives is an essential component of the composition. The derivatives of Niacinamide may be any derivatives. Any derivatives of niacinamide that are having similar property to niacinamide may preferably be used.

Any precursors of niacinamide that are having similar property to niacinamide are also within the scope of the present invention.

The amount of Niacinamide is in the range of 0.1 to 5%, preferably 0.5 to 5%, more preferably 1 to 5% and most preferably 2 to 5% by weight of the composition.

The composition of the present invention also preferably comprises an Antimicrobial peptide (AMP).

The present inventors found that the composition according to the present invention which comprises thymol, terpineol and niacinamide provides a synergistic combination and able to provide antimicrobial benefits as desired.

Antimicrobial peptide (AMP):

AMPs form an integral part of the skin's own defense system. AMPs were initially discovered in insects and in animals and ever since their initial discovery, AMPs are regarded as promising antimicrobials. AMPs are ubiquitous in nature and they typically exhibit a broad spectrum of activity against invading bacteria, fungi, enveloped viruses and parasites (Braff and Gallo, 2006). AMPs are generally short peptides and in humans, about 90 different AMPs are reported to be present. AMPs in general have two major physical features and they are—a) cationic charge and b) a significant proportion of hydrophobic residues. The cationic charge of the AMPs promotes selectivity for negatively charged microbial cytoplasmic membranes whereas the hydrophobicity facilitates interactions with the cell membrane of the microbial species.

The most important groups of human antimicrobial peptides are defensins, histatins, cathelicidin (LL-37), dermcidin, psoriasin and RNAse. Defensins are the more representatives and cathelicidins form the second group of mammalian AMPs.

Recent studies have shown a variety of antimicrobial peptides (AMPs) mimic chemokines and have the capacity to rapidly activate host innate and adaptive immune systems by serving as early warning signals. They are capable of recruiting and activating antigen-presenting cells. These potent immunostimulants include defensins, cathelicidin (LL-37), eosinophil-derived neurotoxin (EDN), and high-mobility group box protein 1 (HMGB1). For example, defensins, LL-37, HMGB1 and EDN mimic chemokine and cytokine activities by interacting with CCR6, FPRL-1 and Toll-like receptors (TLR2) respectively. These antimicrobial peptides are constitutively produced and released by leukocytes, keratinocytes and epithelial cells lining the gastrointestinal, genitourinary and tracheobronchial tree. In addition, they are induced by injurious stimulants and cytokines. These peptides all have in vivo immunoadjuvant effects. These AMPs have now been grouped under the novel term "alarmins", in recognition of their role in rapidly mobilizing the immune system for protection against host damage (Oppenheim and Yang, 2005).

AMP's can also synthetically be prepared.

AMP is one of the most preferred component for the composition of the present invention. The present inventors have found that AMP in combination with Thymol, Terpineol and Niacinamide is able to provide a composition which boosts the synergistic activity at very low concentration of thymol and terpineol.

The most preferred AMP is LL-37 for the purpose of the present invention.

The amount of AMP is preferably in the range from 0.01 to 10, more preferably 0.1 to 5 and most preferably from 1 to 5 μg/g of the composition.

The present inventors have further found that optionally adding AMP in the synergistic antimicrobial composition of the present invention further enhances the antimicrobial benefit.

The synergistic antimicrobial composition of the present invention also comprises a cosmetically acceptable base. The base formulation may be varied depends on the kinds of application.

The composition of the present invention preferably in the form of a leave-on composition. The leave-on composition may be in the form of vanishing cream or may be in the form of a sanitizer composition. The most preferred application being the hand sanitization.

The cosmetically acceptable base is preferably a cream, lotion, gel or emulsion.

Personal care compositions (leave-on) may be prepared using different cosmetically acceptable emulsifying or non-emulsifying systems and vehicles. A highly suitable base is a cream. Vanishing creams are especially preferred. Vanishing cream bases generally comprise 5 to 25% fatty acid and 0.1 to 10% soap. Vanishing cream base gives a highly appreciated matty feel to the skin. C12 to C20 fatty acids are especially preferred in vanishing cream bases, further more preferred being C14 to C18 fatty acids. The most preferred fatty acid is stearic acid. The fatty acid in the composition is more preferably present in an amount in the range of 5 to 20% by weight of the composition. Soaps in the vanishing cream base include alkali metal salt of fatty acids, like sodium or potassium salts, most preferred being potassium stearate. The soap in the vanishing cream base is generally present in an amount in the range of 0.1 to 10%, more preferably 0.1 to 3% by weight of the composition. Generally, the vanishing cream base in personal care compositions is prepared by taking a desired amount of total fatty matter and mixing with potassium hydroxide in desired amounts. The soap is usually formed insitu during the mixing.

An especially suitable cosmetically acceptable base is one which comprises a water-in-oil emulsion comprising silicone oils as the continuous phase. The water in oil emulsions preferably comprise a cross-linked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. The creation of cross-linkages between linear polymers, such as dimethicone, converts the linear polymer into a silicone elastomer. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions. Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer]; EL-8050 [INCI Name: Isododecane (and) Dimethicone/Bis-Isobutyl PPG 20 Crosspolymer] DC 9040, DC9041, DC9045 (Dimethicone crosspolymer); DC 9506, 9509 (Dimethicone vinyl dimethicone crosspolymer); Shin-Etsu KSG-15, KSG-16, KSG-17 (Dimethicone vinyl dimethicone crosspolymer). It is further preferred that the composition comprises 5 to 50% silicone elastomer by weight of the composition.

In the case of wash-off composition, In addition to the essential ingredients as described earlier, preferred embodiments of the cleansing compositions may also include other optional and preferred ingredients for their known benefits. The type and content will largely depend on the nature and type of cleansing composition as well as general principles of formulation science.

Where the composition is in the form of a bar of soap or a liquid soap, it is preferred that the composition contains free fatty acids. Preferred embodiments contain 0.01 wt % to 10 wt % free fatty acid, especially when major portion of the surfactant is soap based. Potentially suitable fatty acids are C8 to C22 fatty acids. Preferred fatty acids are C12 to C18, preferably predominantly saturated, straight-chain fatty acids. However, some unsaturated fatty acids can also be employed. Of course the free fatty acids can be mixtures of shorter chain length (e.g., C10 to C14) and longer chain-length (e.g., C16-C18) chain fatty acids. For example, one useful fatty acid is fatty acid derived from high-laurics triglycerides such as coconut oil, palm kernel oil, and babasu oil. The fatty acid can be incorporated directly or they can be generated in-situ by the addition of a protic acid to the soap during processing. Examples of suitable protic acids include: mineral acids such as hydrochloric acid and sulfuric acid, adipic acid, citric acid, glycolic acid, acetic acid, formic acid, fumaric acid, lactic acid, malic acid, maleic acid, succinic acid, tartaric acid and polyacrylic acid. However, care should be taken that the residual electrolyte in the bar does not substantially reduce the effectiveness of the anticracking agent. The level of fatty acid having a chain length of 14 carbon atoms and below should generally not exceed 5.0%, preferably not exceed about 1% and most preferably be 0.8% or less based on the total weight of the continuous phase.

Water soluble/dispersible polymers is an optional ingredient that is highly preferred to be included in composition. These polymers can be cationic, anionic, amphoteric or nonionic types with molecular weights higher than 100,000 Dalton. They are known to increase the viscosity and stability of liquid cleanser compositions, to enhance in-use and after-use skin sensory feels, and to enhance lather creaminess and lather stability. Amount of the polymers, when present, may range from 0.1 to 10% by weight of the composition.

Examples of water soluble/or dispersible polymers include the carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers such as Aculyn® 28, Aculyn® 22 or Carbopol® Aqua SF1; cationic polymer such as modified polysaccharides including cationic guar available from Rhone Poulenc under the trade name Jaguar® C13S, Jaguar® C14S, Jaguar® C17, or Jaguar® C16; cationic modified cellulose such as UCARE® Polymer JR 30 or JR 40 from Amerchol; N-Hance® 3000, N-Hance® 3196, N-Hance® GPX 215 or N-Hance® GPX 196 from Hercules; synthetic cationic polymer such as Merquat® 100, Merquat® 280, Merquat® 281 and Merquat® 550 sold by Nalco; cationic starches such as StaLok® 100, 200, 300 and 400 sold by Staley Inc.; cationic galactomannans such as Galactasol® 800 series by Henkel, Inc.; Quadrosoft® LM-200; and Polyquaternium-24®. Also suitable are high molecular weight polyethylene glycols such as Polyox® WSR-205 (PEG 14M), Polyox® WSR-N-60K (PEG 45), and Polyox® WSR-301 (PEG 90M).

The composition of the invention may additionally comprise a skin-lightening agent. Apart from niacinamide which is anyway presence as one of the essential component of the present compostion, other well known skin lightening agents e.g. aloe extract, ammonium lactate, arbutin, azelaic acid, kojic acid, butyl hydroxy anisole, butyl hydroxy toluene, citrate esters, 3 diphenyl propane derivatives, 2,5 dihydroxy-benzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxy-caprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof.

Preferably, the composition may have sunscreen. Any sunscreen that can be suitably used with the base may be added. Both, UVA and UVB sunscreens may preferably be added.

The composition of the invention preferably comprises a UV-A sunscreen which is a dibenzoylmethane or its derivatives. Preferred dibenzoylmethane derivatives are selected from 4-tert-butyl-4'-methoxydibenzoylmethane, 2-methyl-dibenzoylmethane, 4-methyl-dibenzoylmethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. The most preferred dibenzoylmethane derivative is 4-tert.-butyl-4'-methoxydibenzoylmethane. The composition of the invention preferably comprises 0.1 to 10%, more preferably 0.2 to 5%, further more preferably 0.4 to 3%, by weight dibenzoylmethane or a derivative thereof based on total weight of the composition and including all ranges subsumed therein.

The composition preferably comprises a UV-B organic sunscreen selected from the class of cinnamic acid, salicylic acid, diphenyl acrylic acid and derivatives thereof. Illustrative non-limiting example of UV-B sunscreens which are commercially available and useful for inclusion in the composition of the invention are Octisalate™, Homosalate™, NeoHelipan™, Octocrylene™, Oxybenzone™ or Parsol MCX™. The UV-B sunscreen is most preferably 2-ethyl-hexyl-4-methoxy cinnamate which is commercially available as Parsol MCX. The UV-B organic sunscreen is preferably included in 0.1 to 10%, more preferably 0.1 to 7% by weight of the composition. It has been observed that presence of an organic UV-B sunscreen like 2-ethyl-hexyl-4-methoxy cinnamate causes further rapid degradation of the UV-A dibenzoylmethane sunscreen in the presence of UV radiation. The presence of the rosmarinic acid ester compound is found to be very efficacious in stabilizing the composition even when UV-B sunscreens are present.

Useful inorganic sun-blocks are also preferably used in the present invention. These include, for example, zinc oxide, iron oxide, silica, such as fumed silica, and titanium dioxide.

Preservatives can also be added into the compositions to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibility between the preservatives and other ingredients. Preservatives are preferably employed in amounts ranging from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide; scrub and exfoliating particles such as polyethylene and silica or alumina; cooling agents such as menthol; skin calming agents such as aloe vera; and colorants. In addition, the compositions may further include 0 to 10% by weight of opacifiers and pearlizers such as ethylene glycol distearate, titanium dioxide or Lytron® 621 (Styrene/Acrylate copolymer); all of which are useful in enhancing the appearance or properties of the product.

Diluents other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Solvents, such as ethyl alcohol, isopropanol, acetone, ethylene glycol monoethyl ether, diethylene glycol monobutyl ether, diethylene glycol monoethyl ether;

In case of soap bars, it may contain particles that are greater than 50 μm in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are talc, calcite, pumice, walnut shells, dolomite and polyethylene.

Advantageously, active agents other than skin conditioning agents defined above may be added to the composition. These active ingredients may be advantageously selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; or mixtures thereof; and the like.

These active agents may be selected from water-soluble active agents, oil soluble active agents, pharmaceutically acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent(s) will vary with the specific active agent, the ability of the active to penetrate through the skin, the age, health condition, and skin condition of the user, and other like factors.

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable base is usually from 10 to 99.9%, preferably from 50 to 99% by weight of the composition, and can, in the absence of other personal care adjuncts, form the balance of the composition.

The composition of the invention may comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition. Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% by weight of the composition and in many instances from 40 to 80%. Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C. Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol. Other than this suitable other vehicle and component used for deodorant composition can be added.

Preferably, when the composition is in the form of a hand sanitizer composition the cosmetically acceptable base may comprises of alcohol and water. The most preferred alcohols are ethyl alcohol and isopropyl alcohol. Even a mixture of two or more alcohol can preferably be used in the hand sanitizer composition. The amount of alcohol preferably in the range of 50 to 95%, more preferably 60 to 80% and most preferably 65 to 80% by weight of the hand sanitizer composition.

The compositions of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, pH adjusters, natural extracts, essential oils, skin sensates, skin soothing agents, and skin healing agents.

The present invention also discloses a method of cleaning or disinfecting a surface comprising the steps of applying a composition according to the invention on to said surface in case of a leave-on composition. This method optionally comprises an additional step of at least partially removing the composition from the surface if it is in the form of a wash-off composition. Preferably the step of at least partially removing the composition is carried out less than 5 minutes after the step of applying the composition on the substrate.

The present invention also discloses a use of a composition of the present invention as disclosed above for improved antimicrobial benefit. Improved antimicrobial benefit preferably means after application of the composition of the present invention the residual microbes on the surface is significantly less. Therefore the composition of the present invention able to provide prolonged/long-lasting antimicrobial benefits. The preferred intended use of the composition of the present invention is non-therapeutic and/or cosmetic.

The present invention also discloses a use of a composition of the present invention as disclosed above for hand hygiene.

Now the invention will be demonstrated by the following non-limiting example.

EXAMPLES

In-vitro Micro-dilution Assay for Determination of Antimicrobial Activity of Different Compositions:

The organism used for the assay was *E. coli* ATCC 10536
The procedure that was followed is given below:
a) First, the bacterial suspension corresponding to $10^6$ cells/mL was prepared in 10 mM Sodium phosphate buffer. For this purpose the sodium phosphate buffer was prepared as follows:
  To prepare the sodium phosphate buffer two different solutions were made. The first solution was prepared by dissolving 27.6 g of $NaH_2PO_4 \cdot H_2O$ (MW=138) in 500 mL of MilliQ water and made up the volume to 1 L with MilliQ water. This was then autoclaved and stored at room temperature. The molarity of the resultant solution was 0.2.
  Then, the second solution was prepared by dissolving 53.62 g of $NaH_2PO_4 \cdot 7H_2O$ (MW=268.1) in 500 mL of MilliQ water and made up the volume to 1 L with MilliQ water. This was then autoclaved and stored at room temperature. The molarity of the resultant solution was 0.2.
  19 mL of the first solution and 81 mL of the second solution was added together followed by the addition of 100 mL of MilliQ water to obtain a 200 mL solution of sodium phosphate buffer of molarity 0.1 with pH 7.4.
  The required level of molarity that was need for the experiments were obtained by diluting the above solution.
b) Then 135 μL/well of the above bacterial suspension was taken and plated in a 96 well microtiter plate.
c) After that 15 μL of 100 mM sodium phosphate buffer was added in all well for all the samples.
d) Then the required test compositions were added in the well for the test.
e) The reaction volume for all the test samples was 300 μL. This reaction volume was adjusted by adding water.
f) The following samples were tested:
  Example A: Only Culture
  Example B: 1% niacinamide
  Example C: 0.01% thymol
  Example D: 0.01% terpineol
  Example E: 0.01% thymol+0.01% terpineol
  Example F: 0.01% Farnesol
  Example G: 0.02% Farnesol
  Example H: 1% niacinamide+0.01% Farnesol
  Example I: 1% niacinamide+0.02% Farnesol
  Example 1: 1% niacinamide+0.01% thymol+0.01% terpineol
  Example 2: 1% niacinamide+1 μg/mL of LL-37+0.01% thymol+0.01% terpineol
For the above purpose, Thymol was procured from Nishant Aromas, India (Purity: 99%), Terpineol was also procured from Nishant Aromas, India (Purity: 99%), LL-37 (AMP) was procured from Sigma (Cat no: 94261),Niacinamide was procured from Veer Chemicals (Purity: 99%) and Farnesol was procured from Sigma-Aldrich (Cat. No: F203).
g) The contact time for the above test (for all the samples) was 4 hours and the temperature was maintained at about 37° C.
h) After the above contact time, the culture was serially diluted and plated on MacConkey Agar Medium (from Difco) and left it for 24 hours. After that, the residual colonies were counted to determine the bacterial kill/ Residual Log.

The results of these experiments are summarized in following Table 1:

TABLE 1

| Example No. | Average Residual Log (CFU/mL) | SE* |
|---|---|---|
| A | 6.41 | 0.04 |
| B | 6.42 | 0.05 |
| C | 6.35 | 0.06 |
| D | 6.45 | 0.06 |
| E | 6.19 | 0.07 |
| F | 6.40 | 0.07 |
| G | 6.35 | 0.04 |
| H | 6.34 | 0.002 |
| I | 6.36 | 0.03 |
| 1 | 5.64 | 0.13 |
| 2 | 3.26 | 0.22 |

*Standard Error

From the above Table it is evident that the residual log for the composition of the present invention (Example 1 and 2) is significantly lesser than the control examples (Examples A to E). It is also clear that the composition that are within the scope of the present invention having better/improved antimicrobial properties than the compositions that are outside the scope of the present invention. It can also be seen from the above table that alone thymol (Example C) and terpineol (Example D) or even a combination of thymol and terpineol (Example E) at low concentration is not effective to provide required antimicrobial action. However, when thymol and terpineol together at this low concentration added with niacinamide (Example 1) and further with LL-37 (Example 2) able to provide good antimicrobial action. It can further be seen from the above table that not all terpene alcohol compounds e.g. Farnesol provides the required benefit when combined with niacinamide.

Human Volunteers Study for Testing Antimicrobial Benefits:

For this purpose, the following leave-on compositions were prepared:

Example J

Base leave-on (lotion) composition: The base leave on composition was prepared as per the following Table 1:

TABLE 2

| Ingredients | Wt % |
| --- | --- |
| Glycerin | 3 |
| Cyclopentasiloxane | 12 |
| PEG-100 Stearate | 0.75 |
| Cetearyl Alcohol | 2 |
| Acrylates Crosspolymers | 3 |
| Preservatives | 0.2 |
| Disodium EDTA | 0.05 |
| Other additives | 3.4 |
| Water | To 100 |

Other additives comprises skin conditioning agent, viscosity modifier, perfume and colour. For the above purpose PEG-100 stearate was obtained from Croda, Acrylates Crosspolymers was obtained from Ganz Chemical, Cetearyl alcohol was obtained from Croda, Cyclopentasiloxane (99%) was obtained from Dow Corning.

Example K

With the base composition of Example J, 0.1 wt % of Thymol and 0.1% Terpineol was added. This amount was adjusted with the water amount in the composition.

Example L

With the base composition of Example J, 2 wt % of Niacinamide was added. This amount was adjusted with the water amount in the composition.

Example 3

With the base composition of Example J, a combination of 0.1 wt % of Thymol, 0.1% Terpineol and 2 wt % of Niacinamide were added. This amount was adjusted with the water amount in the composition.

Testing Protocol:

Nine (9) volunteers were participated in the study with their free consent.

Step 1:

Marketed Lux® soap bar (Non-antimicrobial) was given to each volunteer to use for bathing, washing hands, washing forearms etc. The volunteers were instructed to use only Lux® soap bar and refrain from using any leave on products (sun screen, hand sanitizer, skin moisturizers, lotion, cream, oil, antimicrobial products etc.) for 7 days. On day 8, each volunteer's each volunteer's hands (palm) were washed with Lux® soap by using hand washing protocol given as described below.

For the washing protocol sterile distilled water was used. The temperature of the water was about 25° C. The soap was dipped in the water for about 10 seconds. After that each palms were wetted with about 100 mL of water. Then the wetted soap was applied on the palms for 5 times back and forth across the length of the palm. After that about 5 mL of water was added on the palms and lathered for about 15 seconds. Then the palms were washed with water to remove the soap completely. The excess water was removed by patting dry using sterile tissue paper.

Step 2: An area of 6.25 cm$^2$ area (2.5×2.5 cm) was marked on the inner forearm using a template as given below in the Step 3. Total 4 boxes were made on each forearm with 2 cm gap between each boxes and also a gap of 5 cm from the base of the palm was not used for the study. One marker pen was given to each volunteer to mark the area if it becomes dull or gets erased.

Step 3: The compositions as prepared above (Example A, B and C) were applied on the forearm by following manner:
Area/Box-1: Base formulation of Example J
Area/Box-2: Composition of Example K
Area/Box-3: Composition of Example L
Area/Box-4: Composition of Example 3

Step 3: An aliquot of about 62.5 mg of respective formulations weighed separately in a sterile 35 mm plastic round dishes and were given to the volunteers to apply on the forearm. Volunteers were applied respective formulations on respective delineated spots on the forearm with finger. Used different finger for application of each formulations to avoid the contamination. The formulation was spread over the area for about 60 seconds. After application of each formulation the finger was wiped with sterile tissue paper and also used different finger for each formulations. After about 30 minutes of completing the application of formulations volunteers were collected one set of formulations consisting of about 62.5 mg of each formulation to apply at night (before sleeping).

Step 4: Step 3 was repeated for next 7 days (including 8th day) and volunteers were informed to come to the study site on day 15th without washing there forearm (preferable not taking bath).

Step 5: On day 15, a circular area of 2.54 cm$^2$ is marked with a marker pen inside the each box using a template made from plastic sheet. Then volunteer's forearm were washed with Lux® soap by using the same hand washing protocol given as described above.

Step 6: After washing hands, volunteers were instructed to wait for about 6 hours. The temperature of the room where the volunteers were waiting was about 25° C. and the relative humidity was about 50%. During the entire waiting period the volunteers were informed (a) not to touch the forearm with palm/dress/etc., (b) not to wash or splash water on forearm and (c) not go outside the study premises (e.g. home, work, shopping etc.).

Step 7: After about 6 hours of washing forearm (as described in step 5), 10 μL of test bacterial suspension was added on each circular area inside the box. For this purpose a bacterial culture (about 24 hours old plate culture) of *E. coli* ATCC 10536 corresponding to 5×10$^8$ to 5×10$^9$ cells/mL in 10 mM sterile Sodium phosphate buffer was prepared. After adding the culture, it was spread all over the surface by using pipette tip for about 30 seconds.

Step 8: After about 15 minutes of application of the culture as described in step 7, cups were placed on the circular area and then added 1 mL of sampling buffer inside the cup (cups were made by Teflon and diameter is 1.8 cm). The sampling buffer was phosphate buffer saline (PBS). Then the study instructor was scrubbed on skin inside the cup with the help of Teflon rods (0.3 cm diameter) to recover residual bacteria (as per ASTM E1874-14). The duration of the scrubbing was 1 minute. The recovered residual bacteria were collected in a sterile containers for analysis.

Step 9:

The containers with residual bacteria as collected in Step 8 was analyzed further to determine the amount residual bacteria (Log cfu/palm) using the standard microbiological technique (spread plating on MacConkey agar plates). Then the plates were incubated for about 24 hours at 37° C. After 24 hours the colonies were counted using standard plate counting procedure to determine the Average Residual Log (CFU/mL).

The results of the above study are summarize in following table 3:

TABLE 3

| Example No. | Average Residual Log (CFU/mL) | SE* |
|---|---|---|
| J | 5.14 | 0.03 |
| K | 4.75 | 0.04 |
| L | 3.59 | 0.07 |
| 3 | 2.83 | 0.05 |

*Standard Error

From the above Table it is evident that the residual log for the composition of the present invention (Example 3) is significantly lesser than the control examples (Examples F to H). It is also clear that the composition that are within the scope of the present invention having better/improved antimicrobial properties on human skin than the compositions that are outside the scope of the present invention. For the above table it is further evident that the composition of the present invention provides prolonged/long-lasting antimicrobial benefits.

The invention claimed is:

1. An antimicrobial composition comprising:
    a) thymol;
    b) terpineol;
    c) niacinamide;
    d) an antimicrobial peptide; and
    e) a cosmetically acceptable base.
2. The composition of claim 1, wherein the antimicrobial peptide is LL-37.
3. The composition of claim 1, wherein the amount of thymol is in the range from 0.001 to 5% by weight of the composition.
4. The composition of claim 1, wherein the amount of terpineol is in the range from 0.001 to 5% by weight of the composition.
5. The composition of claim 1, wherein the amount of niacinamide is in the range from 0.1 to 5% by weight of the composition.
6. The composition of claim 1, wherein the amount of antimicrobial peptide is in the range from 0.01 to 10 µg/g of the composition.
7. The composition of claim 1, wherein the composition is in the form of a leave-on composition.
8. The composition of claim 1, wherein the composition is in the form of a wash-off composition.
9. The composition of claim 8, further comprising at least one surfactant.
10. A method of cleaning or disinfecting a surface comprising the step of topically applying an antimicrobial composition on to said surface,
    wherein the composition comprises:
    a) thymol;
    b) terpineol;
    c) niacinamide;
    d) an antimicrobial peptide; and
    e) a cosmetically acceptable base.
11. The method of claim 10, wherein the antimicrobial composition is in the form of a wash-off composition, and wherein there is an additional step of at least partially removing the applied antimicrobial composition.
12. The method of claim 11, wherein the step of at least partially removing the antimicrobial composition is carried out in less than 5 minutes after the step of applying the antimicrobial composition on the surface.
13. The composition of claim 1, wherein the cosmetically acceptable base is a cream, a lotion, a gel, or an emulsion.
14. The composition of claim 1, wherein the cosmetically acceptable base is present in an amount from 10 to 99.9% by weight of the composition.
15. The composition of claim 1, wherein the composition further comprises carvacrol.
16. The composition of claim 1, wherein the antimicrobial peptide comprises defensins, cathelicidin, eosinophil-derived neurotoxin, high-mobility group box protein 1, or a mixture of two or more thereof.

* * * * *